United States Patent
Chung Chan et al.

(10) Patent No.: US 11,508,060 B2
(45) Date of Patent: Nov. 22, 2022

(54) COMPUTER AIDED METHOD AND ELECTRICAL DEVICE FOR ANALYZING FIBROSIS

(71) Applicant: NATIONAL CHENG KUNG UNIVERSITY, Tainan (TW)

(72) Inventors: Pau-Choo Chung Chan, Tainan (TW); Nan-Haw Chow, Tainan (TW); Hung-Wen Tsai, Tainan (TW); Kuo-Sheng Cheng, Tainan (TW); Chun-Cheng Huang, New Taipei (TW)

(73) Assignee: NATIONAL CHENG KUNG UNIVERSITY, Tainan (TW)

(*) Notice: Subject to any disclaimer, the term of this patent is extended or adjusted under 35 U.S.C. 154(b) by 642 days.

(21) Appl. No.: 16/551,703

(22) Filed: Aug. 26, 2019

(65) Prior Publication Data
US 2020/0065965 A1    Feb. 27, 2020

Related U.S. Application Data

(60) Provisional application No. 62/723,460, filed on Aug. 27, 2018.

(30) Foreign Application Priority Data

Aug. 6, 2019  (TW) ................................ 108127947

(51) Int. Cl.
*G06T 7/00* (2017.01)
*G06N 3/08* (2006.01)
(Continued)

(52) U.S. Cl.
CPC ............. *G06T 7/0012* (2013.01); *G06N 3/08* (2013.01); *G06N 20/00* (2019.01); *G06T 7/10* (2017.01);
(Continued)

(58) Field of Classification Search
CPC ................... G06T 7/0012; G06T 7/10; G06T 2207/20084; G06T 2207/30056;
(Continued)

(56) References Cited

U.S. PATENT DOCUMENTS

| 6,738,499 B1 | 5/2004 | Doi et al. |
| 2015/0148658 A1 | 5/2015 | Smith |
| 2016/0260211 A1* | 9/2016 | Gillies ..................... A61B 6/50 |

FOREIGN PATENT DOCUMENTS

| CN | 100486600 C * | 5/2009 |
| CN | 101540051 A | 9/2009 |

(Continued)

OTHER PUBLICATIONS

Donald B. Johnson., "Finding All the Elementary Circuits of a Directed Graph", SIAM Journal on Computing, vol. 4, No. 1, Mar. 1975, 8 pages.

(Continued)

*Primary Examiner* — Amandeep Saini
(74) *Attorney, Agent, or Firm* — CKC & Partners Co., LLC

(57) ABSTRACT

A computer aided method for analyzing fibrosis is provided. First, a segmentation algorithm is performed on a medical image to obtain a segmentation image. Circular fibrosis is detected according to the segmentation image to determine a score. In some cases, it is also necessary to determine a number of fibrosis bridges and the condition of fiber expansion.

15 Claims, 9 Drawing Sheets

(51) Int. Cl.
*G06N 20/00* (2019.01)
*G06T 7/10* (2017.01)
*G16H 50/20* (2018.01)
*G06K 9/62* (2022.01)
*G16H 50/30* (2018.01)

(52) U.S. Cl.
CPC ........... *G16H 50/20* (2018.01); *G06K 9/6292* (2013.01); *G16H 50/30* (2018.01)

(58) Field of Classification Search
CPC . G06T 7/11; G06N 3/08; G06N 20/00; G06N 3/0454; G16H 50/20; G16H 50/30; G16H 30/40; G06K 9/6292; G06K 9/6272; G06V 2201/03; G06V 10/255; G06V 10/454; G06V 10/82
USPC ........................................................ 600/529
See application file for complete search history.

(56) References Cited

FOREIGN PATENT DOCUMENTS

| | | |
|---|---|---|
| CN | 107103187 A | 8/2017 |
| CN | 107895368 A | 4/2018 |
| CN | 108426862 A | 8/2018 |
| TW | 200922627 A | 6/2009 |
| WO | 2006/042864 A1 | 4/2006 |

OTHER PUBLICATIONS

Marco Masseroli et al., "Automatic quantification of liver fibrosis: design and validation of a new image analysis method: comparison with semi-quantitative indexes of fibrosis", Journal of Hepatology, 2000; 32: pp. 453-464.
Christophe Pilette et al., "Histopathological evaluation of liver fibrosis: quantitative image analysis vs semi-quantitative scores", Journal of Hepatology, 1998; 28: pp. 439-446.
Shin'ya Yoshino et al., "Quantitative Evaluation of Hepatic Fibrosis in Biopsy Specimens of Chronic Hepatitis," The Transactions of the Institute of Electrical Engineers of Japan, Nov. 20, 1995, pp. 1460-1467, vol. 115-C, No. 12.
Takuya Kitani et al., "Extraction of fibers and nuclear positions in hepatic histopathlogic images using dark filed imaging," Forum on Information Technology 2008 (The Seventh information technology forum), Aug. 20, 2008, pp. 455-456, vol. 2.
Jhong-Chen Lu, "Basin Geomorphological System", Dalian Press, May 1991.
Jia Tong et al., "Computer-aided Detection Scheme for Lung Nodule Based on HRCT Images", Journal of System Simulation, pp. 3849-3852, vol. 20 No. 14, Jul. 2008.

\* cited by examiner 610   620

COMPUTER AIDED METHOD AND ELECTRICAL DEVICE FOR ANALYZING FIBROSIS

RELATED APPLICATIONS

This application claims priority to U.S. Provisional Application Ser. No. 62/723,460 filed Aug. 27, 2018, and Taiwan Application Serial Number 108127947, filed Aug. 6, 2019, the disclosures of which are incorporated herein by reference in their entireties.

BACKGROUND

Field of Invention

The present invention relates to a computer aided method for analyzing fibrosis to objectively calculate a score.

Description of Related Art

Liver fibrosis is a common change in patients with chronic B or C liver, and will gradually progress to cirrhosis and liver cancer. How to diagnose the degree of the liver fibrosis and give appropriate treatment is an important issue to prevent disease progression. However, the conventional method of fibrosis scoring relies on the subjective judgment of doctors, and so how to provide an objective computer-aided scoring method is of concern to technicians in this field.

SUMMARY

Embodiments of the invention provide an electrical device including a memory configured to store instructions and a processor configured to execute the instructions to perform steps: obtaining a medical image, and performing a segmentation algorithm to the medical image to obtain a segmentation image having at least one fibrosis portion and at least one cell portion; detecting circular fibrosis according to the segmentation image; and determining a score according to a size of the circular fibrosis.

In some embodiments, the step of detecting the circular fibrosis according to the segmentation image includes: performing at least one erosion procedure to the at least one cell portion to obtain at least one portion which is at least partially enclosed by fibrosis; calculating an enclosed degree of the at least one enclosed portion; and determining that the at least one enclosed portion is the circular fibrosis if the enclosed degree of the at least one enclosed portion is greater than a first threshold. The enclosed degree indicates that how the enclosed portion is similar to circles or ovals.

In some embodiments, a roundness of the at least one enclosed portion is calculated to reduce false positives. The roundness is calculated according to the following equation (1) where $f_{circ}$ is the roundness, A is an area of the at least one enclosed portion, and P is a perimeter of the at least one enclosed portion. If the roundness is greater than the first threshold, the at least one enclosed portion is determined to be the circular fibrosis.

$$f_{circ}=4\pi A/p2 \qquad (1)$$

In some embodiments, the step of determining the score according to the size of the circular fibrosis includes: dividing a total area of the circular fibrosis by a total area of the at least one cell portion to obtain a first ratio; and determining that the score is a first score if the first ratio is greater than or equal to a second threshold, otherwise determining that the score is a second score, wherein the first score is greater than the second score.

In some embodiments, the steps further include: detecting portal areas and central veins in the medical image; calculating a number of fibrosis bridges among the portal areas and the central veins according to the segmentation image; and determining that the score is a third score or a fourth score according to the number of the fibrosis bridges.

In some embodiments, the step of calculating the number of the fibrosis bridges among the portal areas and the central veins according to the segmentation image includes: taking the portal areas and the central veins as nodes; performing a triangulation algorithm to the nodes to determine adjacent nodes of each of the nodes; and for each of the nodes, determining if the node is connected to the corresponding adjacent nodes through the at least one fibrosis portion in the segmentation image so as to calculate the number of the fibrosis bridges. The step of determining that the score is the third score or the fourth score according to the number of the fibrosis bridges includes: determining if a second ratio of the number of the fibrosis bridges to an edge number is greater than a third threshold; and determining that the score is the third score if the second ratio is greater than the third threshold, otherwise determining that the score is the fourth score, wherein the third score is greater than the fourth score, the edge number is (3n−3−k), n is a number of the nodes, and k is a number of the nodes on a convex hull formed by the nodes.

In some embodiments, the step of calculating the number of fibrosis bridges among the portal areas and the central veins according to the segmentation image: taking the portal areas and the central veins as nodes, and taking distances between the nodes as edges to form a graph; transforming the graph into a tree structure which indicates corresponding adjacent nodes of each of the nodes; and for each of the nodes, determining if the node is connected to the corresponding adjacent nodes through the at least one fibrosis portion in the segmentation image so as to calculate the number of the fibrosis bridges. The step of determining that the score is the third score or the fourth score according to the number of the fibrosis bridges includes: determining if a second ratio of the number of the nodes connected by the fibrosis bridges to a number of all of the nodes is greater than a third threshold; and determining that the score is the third score if the second ratio is greater than the third threshold, otherwise determining that the score is the fourth score, wherein the third score is greater than the fourth score.

In some embodiments, the steps further include: for each of the portal areas, determining if a third ratio of an area of the at least one fibrosis portion in the portal area to an area of the portal area is greater than a fourth threshold, and determining that the portal area is a portal expansion if the third ratio is greater than the fourth threshold; and determining that the score is a fifth score, a sixth score, or a seventh score according to a number of the portal expansions.

In some embodiments, the steps further include: determining that the score is the fifth score if a fourth ratio of the number of the portal expansions to a number of the portal areas is greater than a fifth threshold; determining that the score is the sixth score if the fourth ratio is less than or equal to the fifth threshold and greater than zero; and determining that the score is the seventh score if the number of the portal expansions is equal to zero, wherein the fifth score is greater than the sixth score which is greater than the seventh score.

From another aspect, embodiments of the invention provide a computer aided fibrosis analyzing method for an electrical device. The computer aided fibrosis analyzing method includes: obtaining a medical image, and performing a segmentation algorithm to the medical image to obtain a segmentation image having at least one fibrosis portion and at least one cell portion; detecting circular fibrosis according to the segmentation image; and determining a score according to a size of the circular fibrosis.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. in the specification should be understood for identifying units or data described by the same terminology, but are not referred to particular order or sequence.

Figure 1:
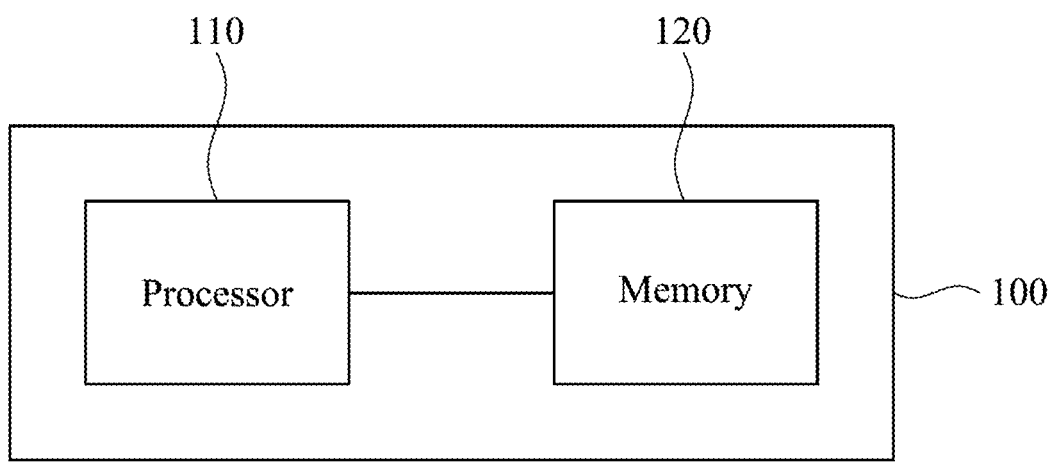
FIG. 1 is a schematic diagram illustrating an electrical device in accordance with an embodiment.

FIG. 1 is a schematic diagram illustrating an electrical device in accordance with an embodiment. Referring to FIG. 1, an electrical device 100 may be a smart phone, a tablet, a personal computer, a notebook computer, a server, an industrial computer, or any electrical device or medical equipment having computing ability, which is not limited in the invention. The electrical device 100 includes a processor 110 and a memory 120. The processor 110 may be a central processing unit, a microprocessor, a microcontroller, a digital signal processor, an image processing chip, an application-specific integrated circuit, etc. The memory 120 may be a volatile memory or a non-volatile memory storing instructions that are executed by the processor 110 to perform a computer aided fibrosis analyzing method. The Ishak score is described as the following table 1.

TABLE 1

| Description | Score |
| --- | --- |
| No fibrosis | 0 |
| Fibrous expansion of some portal areas ± short fibrous septa | 1 |
| Fibrous expansion of most portal areas ± short fibrous septa | 2 |
| Fibrous expansion of most portal areas with occasional portal to portal bridging | 3 |
| Fibrous expansion of portal areas with marked bridging (portal to portal (P-P) as well as portal to central (P-C)) | 4 |
| Marked bridging (P-P and/or P-C) with occasional nodules (incomplete cirrhosis) | 5 |
| Cirrhosis, probable or definite | 6 |

Figure 2A:
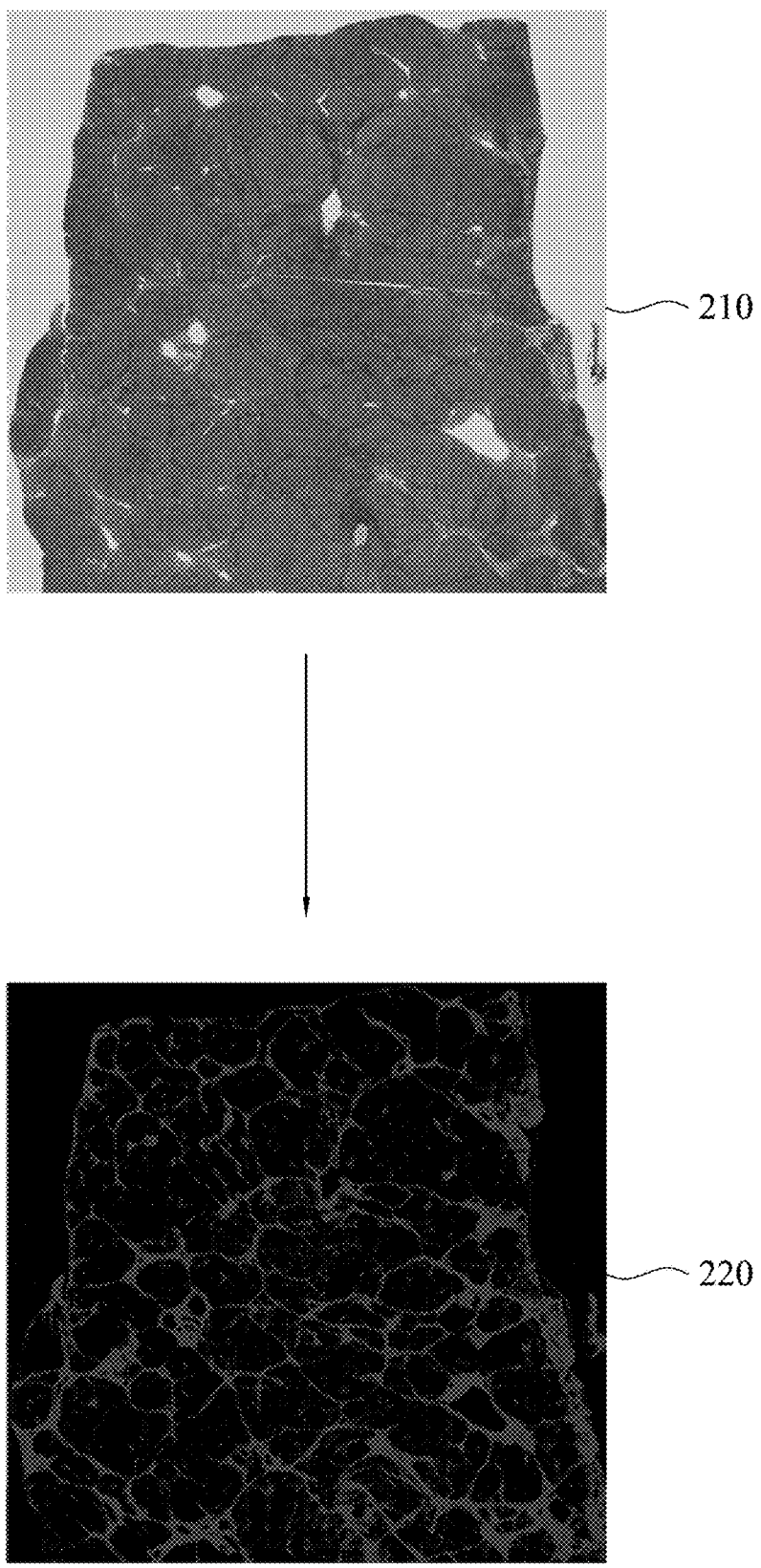
FIG. 2A and FIG. 2B is schematic diagrams illustrating a medical image and a segmentation image in accordance with some embodiments.
Figure 2B:
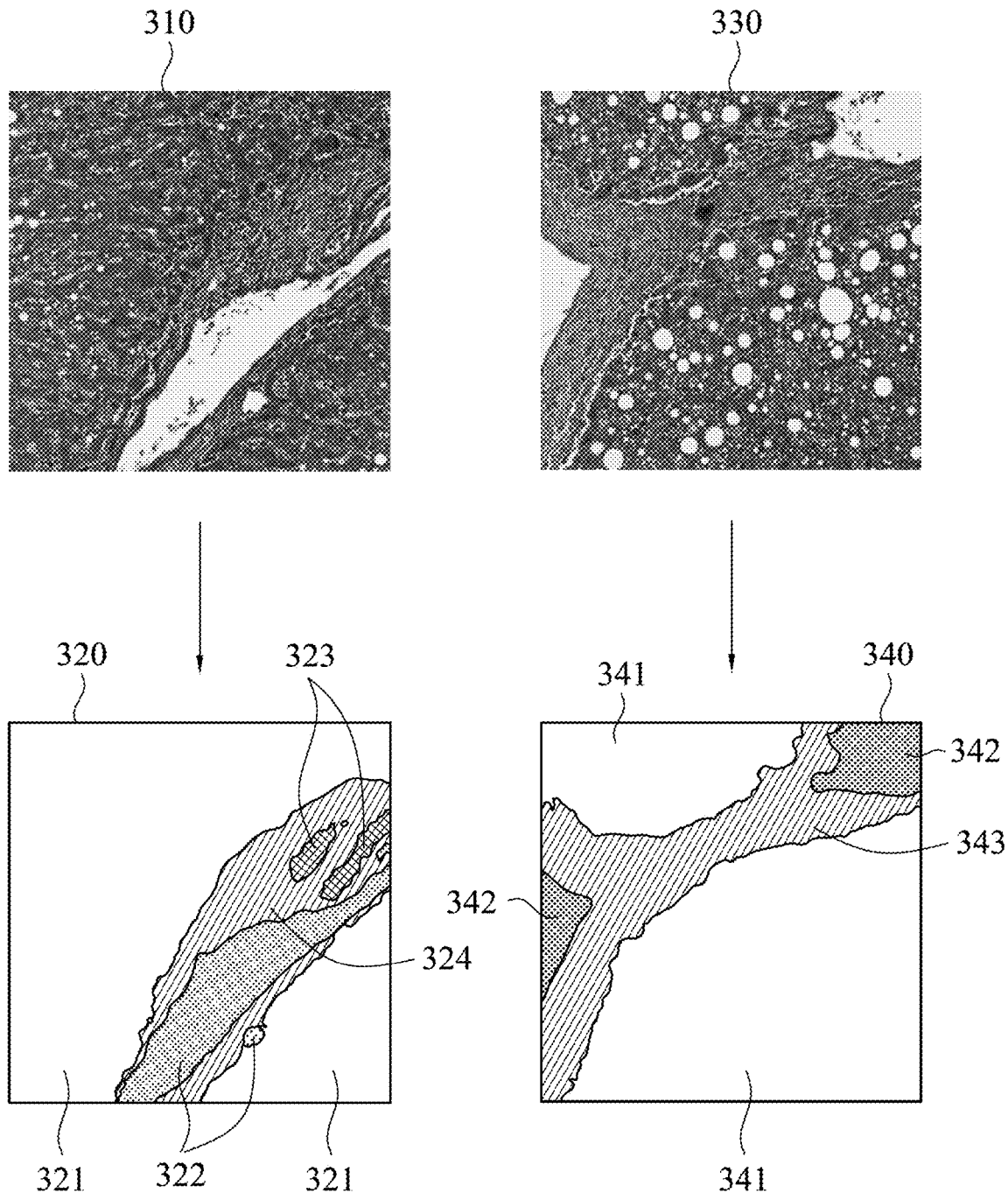

The fibrosis score of Table 1 depends on the doctor's subjective judgement. An objective fibrosis scoring method is provided below. First, a medical image is obtained. In the example of FIG. 2, a medical image 210 is a slice image of a liver tissue, but slice images of other organs may be adopted in other embodiments, which are not limited in the invention. A segmentation algorithm is performed to the medical image 210 to obtain a segmentation image 220 which is a binary image to show whether a pixel is fibrosis. In some embodiments, the segmentation algorithm is a convolutional neural network (CNN), but other algorithms may be adopted. In the training phase, the input of the CNN is unsegmented medical images, and the output of the CNN is manually labeled binary images. In the test phase, the medical image 210 is inputted to a trained CNN to output the segmentation image 220. The segmentation image 220 is binary (i.e. indicating two classes) in the embodiment, but the segmentation image may have more classes in other embodiments. For example, referring to FIG. 2B, a medical image 310 and a medical image 330 are slice images of liver tissues. A segmentation image 320 is the segmentation result of the medical image 310, and a segmentation image 340 is the segmentation result of the medical image 330. The segmentation image 320 includes cell portions 321, vessel portions 322, bile-duct portions 323, and fibrosis portions 324. The segmentation image 340 includes cell portions 341, vessel portions 342, and a fibrosis portion 343. The number and the types of the classes segmented by the segmentation algorithm are not limited in the invention.

Figure 3:
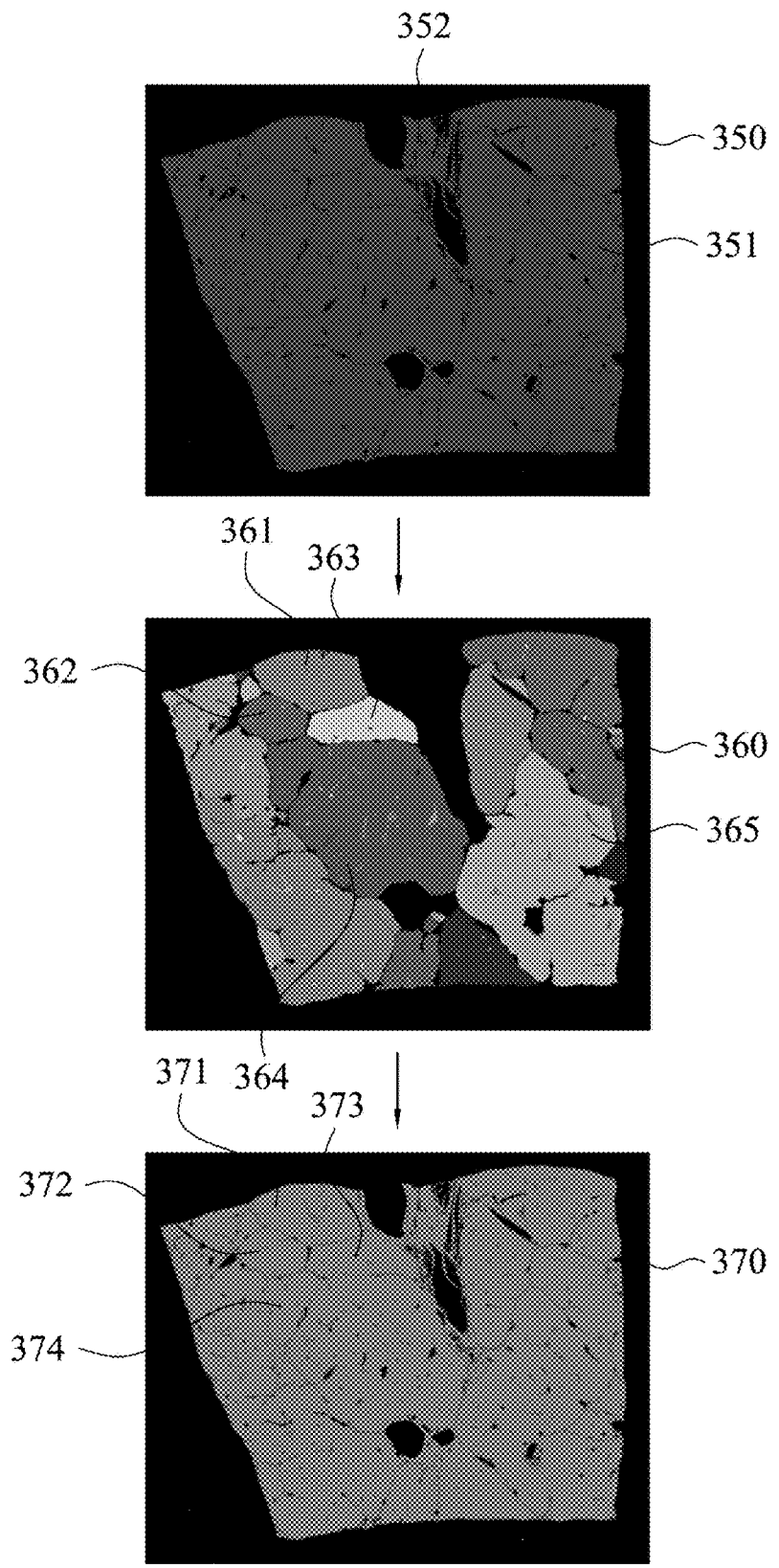
FIG. 3 is a schematic diagram for detecting a circular fibrosis in accordance with an embodiment.

Next, circular fibrosis is detected according to the segmentation image. The circular fibrosis means the liver cells surrounded by fibrosis, and it is also called "nodule". Since the cell portions and the fibrosis portions have been found in the segmentation image, the cell portions are left in the circular fibrosis if the fibrosis portion is excluded. The shape of the left cell portions would be close to a circle or an oval. However, this approach only identifies the liver cells which are completely surrounded by the fibrosis. A practical approach is to identify circular fibrosis if more than a percentage (e.g. 75%) of the liver cells are surrounded. Therefore, in the embodiment, an erosion procedure of image processing is performed to the cell portions after the fibrosis portions are excluded from the segmentation image to obtain enclosed portions. If more than 75% of the liver cells are surrounded by the fibrosis in an area, then the erosion procedure will remove some protruding liver cells so that the remaining liver cells are independent (i.e. not connected to other liver cells). Referring to FIG. 3, a segmentation image 350 includes cell portions 351 and fibrosis portions 352. An image 360 is obtained after excluding the fibrosis portions 352 and performing the erosion procedure to the cell portions 351. Different grey levels are used to indicate each of enclosed portions (e.g. enclosed portions 361-365).

Next, a roundness of each enclosed portion is calculated. If the roundness is greater than a threshold, it is determined that the enclosed portion is circular fibrosis. In some embodiments, the roundness is calculated by the following equation (1).

$$f_{circ} = 4\pi A/p2 \qquad (1)$$

$f_{circ}$ is the roundness. A is the area of the enclosed portion. P is the perimeter of the enclosed portion. The greater the roundness is, the more the enclosed portion is close to a circle. In the embodiment, when the long axis of the enclosed portion (i.e. the longest distance between two points in the portion) is greater than 1 cm and the roundness is greater than 0.3, then it is determined that the enclosed portion is the circular fibrosis. For example, the image 370 shows circular fibrosis 371-374 while the other enclosed portions are not circular fibrosis. In some embodiments, multiple times of erosion procedures with different kernels are performed to the cell portions 351 after the fibrosis portions 352 are excluded, and the roundness is calculated for each time the erosion procedure is performed to determine if the enclosed portion is the circular fibrosis. The union of all determination results for one enclosed portion is taken as the final output. That is, if one enclosed portion is determined to be circular fibrosis in any one of the erosion procedures, then this enclosed portion is determined to be the circular fibrosis. The erosion procedure is performed for multiple times because the enclosed portion 361-365 may not be found by performing a single erosion procedure with a small kernel while the liver cells between the enclosed portion 361-365 are not cut off.

After the circular fibrosis is detected, the size of the circular fibrosis is used to determine that a score is 5 or 6. To be specific, a total area of the circular fibrosis 371-374 is divided by a total area of all cell portions 351 in the segmentation image to obtain a ratio. If the ratio is greater than or equal to a threshold, then the score is 6, otherwise the score is 5.

Figure 4:
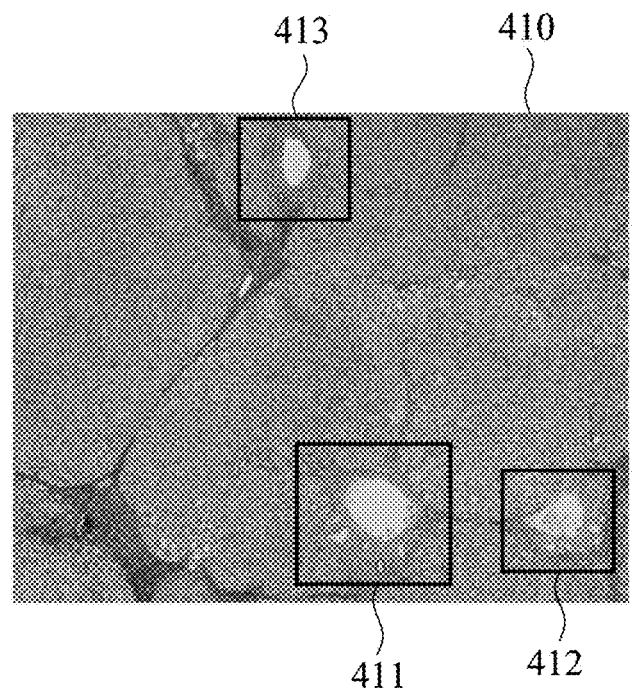
FIG. 4 to FIG. 6 are schematic diagrams illustrating portions of the medical image in accordance with an embodiment.

If the medical image does not contain circular fibrosis, then the score is in the range of 0 to 4. When the fibrosis situation is serious, fibrosis bridges are generated among portal areas and central veins, resulting in that the score is 3 or 4. If there is no fibrosis bridge, the score is in the range of 0 to 2. Accordingly, the portal areas and the central veins are detected in the medical image 210. For example, the detected portal areas and central veins are surrounded by bounding boxes as shown in FIG. 4 in which a partially enlarged medical image 410 includes portal areas 411-413. Note that the detection may be performed by any image analysis method or any machine learning algorithm such as CNN, support vector machine, etc. which is not limited in the invention. In some embodiments, a single machine learning model is trained to detect both of the portal areas and the central veins. In some embodiments, two machine learning models are trained separately to detect the portal areas and the central veins.

The situation of no fibrosis bridge is described herein. In this case, it is determined if each portal area is a fibrosis expansion. To be specific, for each of the portal areas, it is determined if a ratio of the area of the fibrosis portion to the area of the portal area is greater than a threshold (e.g. 50%).

Figure 5:
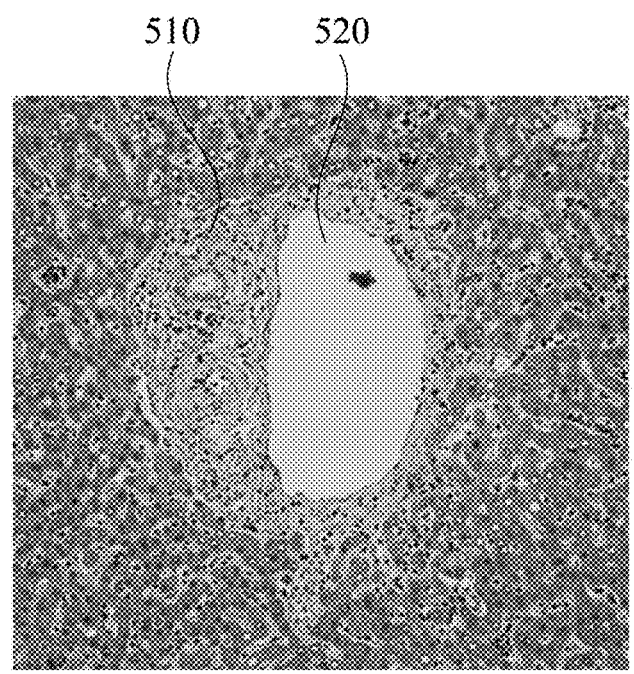
Figure 6:
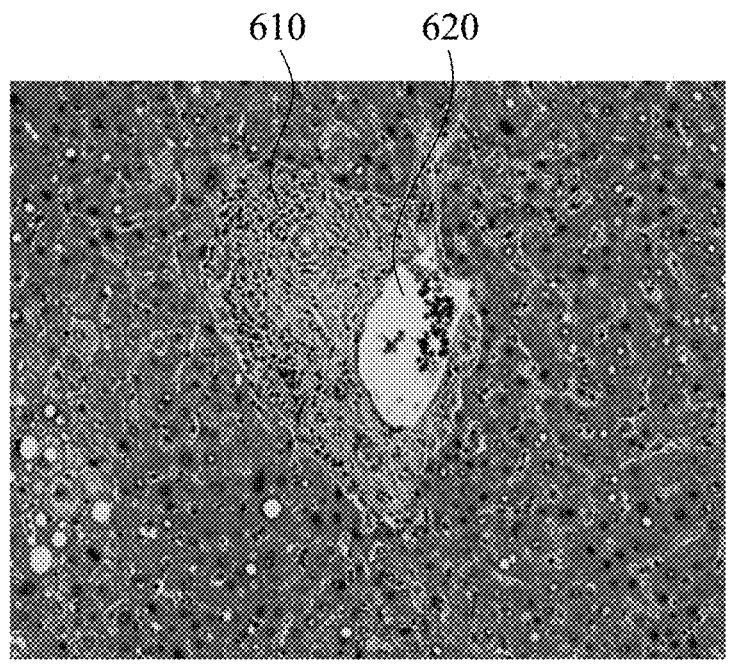

If the determination result is affirmative, it is determined that the portal area is the portal expansion. Note that the area of the portal area is the sum of the area of the fibrosis portion and the area of the vessel portion or the cell portion, and all these areas can be calculated based on the segmentation image. For example, in the example of FIG. 5, the portal area includes a fibrosis portion 510 and a non-fibrosis portion 520. The ratio of the area of the fibrosis portion 510 to the area of the whole portal area is not greater than 50%, and therefore this portal area is not the portal expansion. In the example of FIG. 6, the portal area includes a fibrosis portion 610 and a non-fibrosis portion 620. The ratio of the fibrosis portion 610 to the area of the whole portal area is greater than 50%, and therefore this portal area is the portal expansion.

If a ratio of the number of the portal expansions to the number of all portal areas is greater than a threshold (e.g. 50%), it is determined that the score is 2. If the ratio is less than or equal to 50% and greater than another threshold (e.g. 0, 1, 2, or other suitable values), it is determined that the score is 1; and if the number of the portal expansion is less than or equal to the threshold (e.g. 0), the score is 0. These thresholds can be adjusted with respect to the adopted algorithms, and any value of the thresholds is in the scope of the disclosure.

Figure 7:
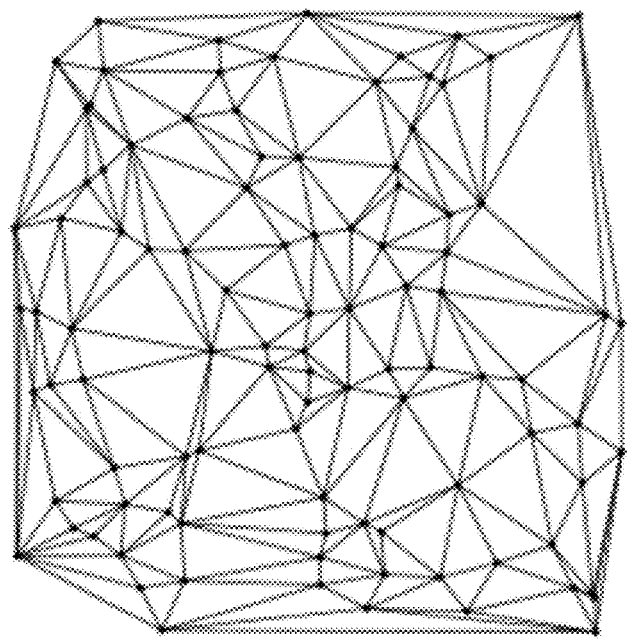
FIG. 7 is a schematic diagram illustrating triangulation in accordance with an embodiment.

The fibrosis bridge is described herein. When the condition of fibrosis is serious, the fibrosis of the portal areas or central veins is expanded into adjacent portal area or central vein to form the fibrosis bridge. The number of the fibrosis bridges between two portal areas, between two central veins, and between one portal area and one central vein are counted herein. In detail, all the portal areas and the central veins in the medical image are taken as nods. A triangulation algorithm is performed to the nodes to form a graph which includes the nodes and edges as shown in FIG. 7. The triangulation algorithm is, for example, Delaunay Triangulation, but the invention is not limited thereto. After the triangulation algorithm is performed, each node is connected to adjacent nodes through edges of the corresponding triangles. For each node, it is determined if the node is connected to the adjacent nodes through the fibrosis portions of the segmentation image. For example, referring to FIG. 8, nodes 801-808 are shown in the segmentation image to see if there are fibrosis bridges between the nodes 801-808. Each of the nodes 801-808 represents one portal area or one central vein, and the coordinates of the nodes 801-808 are the central points of the corresponding bounding boxes. Take the node 804 as an example, the node 804 is adjacent to the nodes 801, 806, 808, and 805 based on the triangulation result. There is no fibrosis bridge between the node 804 and the node 801, but there are fibrosis bridges between the node 804 and the nodes 805, 806, 808 (three of fibrosis bridges are counted). In other words, the greater the number of the fibrosis bridges is, the more serious of the fibrosis situation will be. The determination of the bridges is performed by the algorithm of Breadth-first Search (BFS), but other suitable algorithms may be adopted to determine if two nodes are connected through a fibrosis bridge.

Figure 9:
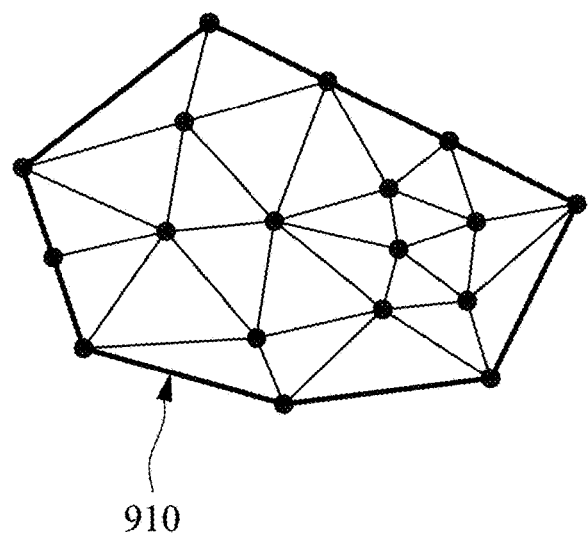
FIG. 9 is a schematic diagram of a convex hull formed by nodes after the triangulation algorithm is performed in accordance with an embodiment.

FIG. 9 is a schematic diagram of a convex hull formed by nodes after the triangulation algorithm is performed in accordance with an embodiment. Total of (2n−2−k) triangles and (3n−3−k) edges are formed after the triangulation algorithm is performed where n is the number of the nodes and k is the number of the nodes on a convex hull 910 formed by the nodes. (3n−3−k) is also referred to an edge number, and (2n−2−k) is also referred to a triangle number. The aforementioned step of determining if the nodes are connected through fibrosis is to check whether these (3n−3−k) edges are fibrosis bridges. If the ratio of the number of the fibrosis bridges to the edge number (3n−3−k) is less than a threshold (e.g. 50%), then the score is 3, otherwise the score is 4.

In some embodiments, the portal areas and the central veins are taken as nodes, and distances between the nodes are taken as edges to form a fully connected graph. The fully connected graph is transformed into a tree structure (e.g. mining spanning three or other three structures) indicating adjacent nodes of each of the nodes. For each of the nodes, it is determined if the node is connected to the corresponding adjacent nodes through the fibrosis portions to calculate the number of the fibrosis bridges. In some embodiments, the number of the fibrosis bridges is divided by the number of the nodes (i.e. the positive integer n) to get a ratio. If the ratio is greater than a threshold, then the score is 4, otherwise the score is 3. In some embodiments, if a ratio of the number of the nodes connected by the fibrosis bridges to the number of all of the nodes is greater than a threshold, then the score is 4, otherwise the score is 3.

The scores of 0-6 are merely examples, and the scores may have other values, symbols, or texts, which are not limited in the invention. From another aspect, the scores of 0-6 are also referred to a seventh score to a first score, but the values, symbols, or texts that the first to seventh scores represent are not limited in the invention.

Figure 8:
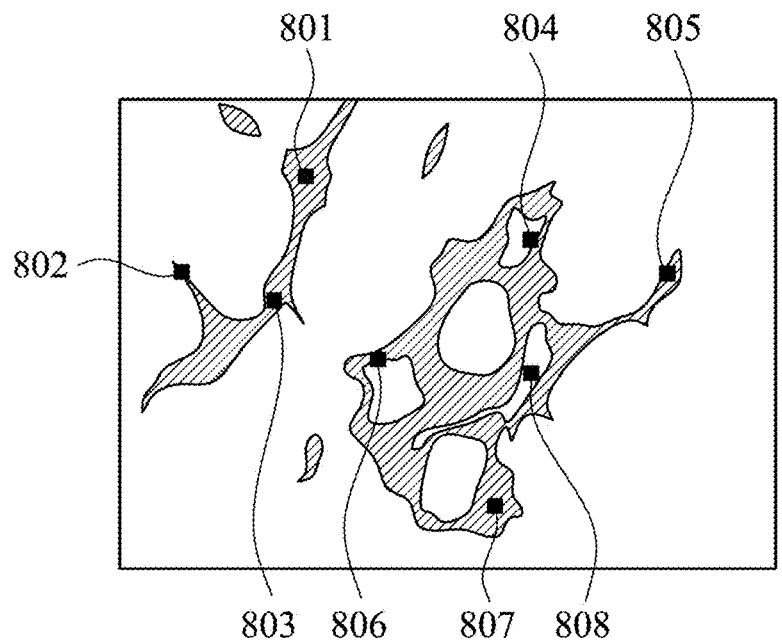
FIG. 8 is a schematic diagram illustrating nodes of the segmentation image in accordance with an embodiment.
Figure 10:
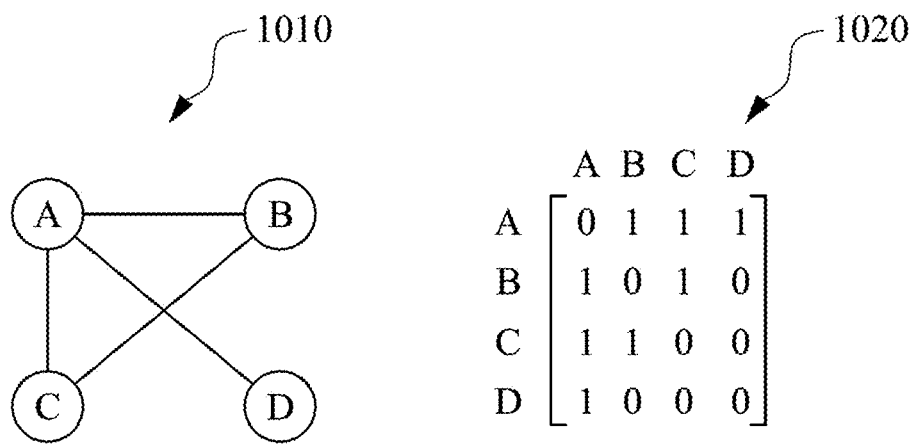
FIG. 10 is a schematic diagram illustrating a connection matrix in accordance with an embodiment.

In some embodiments, the circular fibrosis may be detected by the fibrosis bridges because the nodes are connected to form a cycle through the fibrosis. For example, as shown in FIG. 8, nodes 804, 806 and 808 form a cycle. In order to count the number of the cycles, the adjacent relationship between the nodes is used to create a connection matrix. For example, FIG. 10 illustrates a graph 1010 includes nodes of the portal areas and the central veins. Each edge of the graph 1010 indicates a fibrosis bridge. A connection matrix 1020 is created according to the nodes and edges of the graph 1010. For example, there is a fibrosis edge the node A and the node B, but there is no fibrosis edge between the node B and the node D, and so on. The cycles are detected according to the connection matrix 1020, for example, by the thesis "Finding All the Elementary Circuits of a Directed Graph" by D. B. Johnson, 1975, but the invention is not limited thereto.

Figure 11:
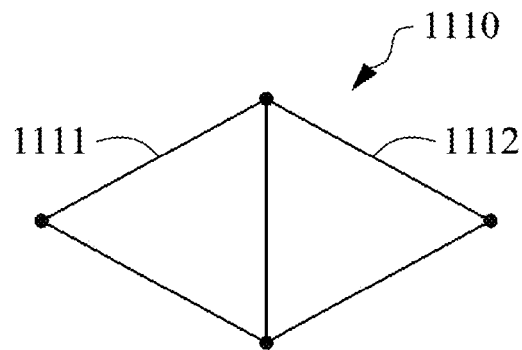
FIG. 11 is a schematic diagram of cycles in accordance with an embodiment.

FIG. 11 is a schematic diagram of cycles in accordance with an embodiment. There are three cycles 1110-1112 in the example of FIG. 11 in which the cycle 1110 has four nodes, and each of the cycle 1111 and the cycle 1112 has three nodes. Note that the union of the cycle 1111 and cycle 1112 constitutes the cycle 1110. The result of the Johnson algorithm produces four cycles, but it would repeat the calculation of the circular fibrosis. Therefore, the repeated cycles have to be excluded. To be specific, for each cycle, it is determined if the cycle is the union of other cycles as written in the following equation (2).

$$C_i = U_{j, j \neq i} C_j \quad (2)$$

$C_i$ and $C_j$ are $i^{th}$ and $j^{th}$ cycles respectively. If the equation (2) is true, the cycle $C_i$ is deleted. After all cycles are tested by the equation (2), the number of the remaining cycles is referred to a cycle number. For example, in the embodiment of FIG. 11, the cycle 1110 is deleted, and only the cycles 1111 and 1112 are counted. From another aspect, this step of searching cycles and deleting repeated cycles is to find a triangle formed by the fibrosis from the aforementioned (2n−2−k) triangles. Next, it is determined if a ratio of the cycle number to the number of the triangles (2n−2−k) is less than a threshold (e.g. 50%). If the determination is affirmative, the score is 5, or otherwise the score is 6.

Figure 12:
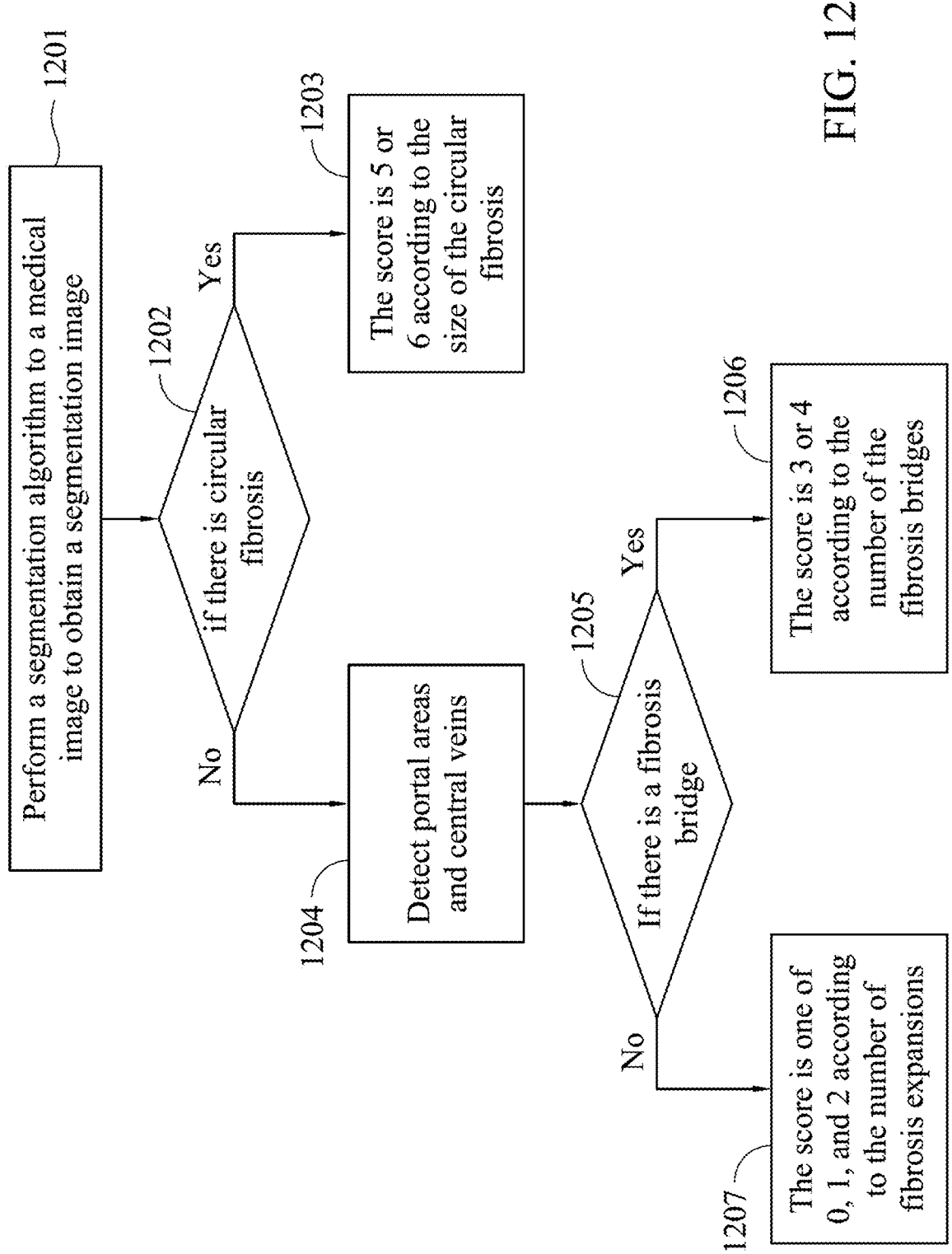
FIG. 12 is a flow chart of a computer aided fibrosis analyzing method in accordance with an embodiment.

FIG. 12 is a flow chart of a computer aided fibrosis analyzing method in accordance with an embodiment. In step 1201, a segmentation algorithm is performed to a medical image to obtain a segmentation image. In step 1202, it is determined if there is circular fibrosis. If the circular fibrosis exists, in step 1203, it is determined that the score is 5 or 6 according to the size of the circular fibrosis. If there is no circular fibrosis, in step 1204, portal areas and central veins are detected. In step 1205, it is determined if there is a fibrosis bridge. If there is a fibrosis bridge, in step 1206, it is determined the score is 3 or 4 according to the number of the fibrosis bridges. If there is no fibrosis bridge, in step 1207, it is determined that the score is one of 0, 1, and 2 according to the number of fibrosis expansions. However, all the steps in FIG. 12 have been described in detail above, and therefore the description will not be repeated. Note that the steps in FIG. 12 can be implemented as program codes or circuits, and the disclosure is not limited thereto. In addition, the method in FIG. 12 can be performed with the aforementioned embodiments, or can be performed independently. In other words, other steps may be inserted between the steps of the FIG. 12.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An electrical device, comprising:
   a memory, configured to store a plurality of instructions; and
   a processor, configured to execute the instructions to perform a plurality of steps:
      obtaining a medical image, and performing a segmentation algorithm to the medical image to obtain a segmentation image having at least one fibrosis portion and at least one cell portion;
      detecting circular fibrosis according to the segmentation image;
      detecting a plurality of portal areas and a plurality of central veins in the medical image;
      taking the portal areas and the central veins as a plurality of nodes;
      performing a triangulation algorithm to the nodes to determine adjacent nodes of each of the nodes; and
      for each of the nodes, determining if the node is connected to the corresponding adjacent nodes through the at least one fibrosis portion in the segmentation image so as to calculate a number of the fibrosis bridges; and
      determining a score according to a size of the circular fibrosis and the number of the fibrosis bridges.

2. The electrical device of claim 1, wherein the step of detecting the circular fibrosis according to the segmentation image comprises:
   excluding the at least one fibrosis portion, and performing at least one erosion procedure to the at least one cell portion to obtain at least one enclosed portion;

calculating a roundness of the at least one enclosed portion; and determining that the at least one enclosed portion is the circular fibrosis if the roundness of the at least one enclosed portion is greater than a first threshold.

3. The electrical device of claim 2, wherein the roundness is calculated according to a following equation (1):

$$f_{circ}=4\pi A/p2 \qquad (1)$$

wherein $f_{circ}$ is the roundness, A is an area of the at least one enclosed portion, and P is a perimeter of the at least one enclosed portion.

4. The electrical device of claim 1, wherein the step of determining the score according to the size of the circular fibrosis and the number of the fibrosis bridges comprises:

dividing a total area of the circular fibrosis by a total area of the at least one cell portion to obtain a first ratio; and determining that the score is a first score if the first ratio is greater than or equal to a second threshold, otherwise determining that the score is a second score, wherein the first score is greater than the second score.

5. The electrical device of claim 1, wherein the step of determining the score according to the size of the circular fibrosis and the number of the fibrosis bridges comprises:

determining if a second ratio of the number of the fibrosis bridges to an edge number is greater than a third threshold; and determining that the score is a third score if the second ratio is greater than the third threshold, otherwise determining that the score is a fourth score, wherein the third score is greater than the fourth score, the edge number is (3n−3−k) n is a number of the nodes, and k is a number of the nodes on a convex hull formed by the nodes.

6. The electrical device of claim 1, wherein the steps further comprise:

for each of the portal areas, determining if a third ratio of an area of the at least one fibrosis portion in the portal area to an area of the portal area is greater than a fourth threshold, and determining that the portal area is a portal expansion if the third ratio is greater than the fourth threshold; and determining that the score is a fifth score, a sixth score, or a seventh score according to a number of the portal expansions.

7. The electrical device of claim 6, wherein the steps further comprise:

determining that the score is the fifth score if a fourth ratio of the number of the portal expansions to a number of the portal areas is greater than a fifth threshold;

determining that the score is the sixth score if the fourth ratio is less than or equal to the fifth threshold and greater than zero; and determining that the score is the seventh score if the number of the portal expansions is equal to zero, wherein the fifth score is greater than the sixth score which is greater than the seventh score.

8. A computer aided fibrosis analyzing method for an electrical device, wherein the computer aided fibrosis analyzing method comprises:

obtaining a medical image, and performing a segmentation algorithm to the medical image to obtain a segmentation image having at least one fibrosis portion and at least one cell portion;

detecting circular fibrosis according to the segmentation image;

detecting a plurality of portal areas and a plurality of central veins in the medical image;

taking the portal areas and the central veins as a plurality of nodes;

performing a triangulation algorithm to the nodes to determine adjacent nodes of each of the nodes; and for each of the nodes, determining if the node is connected to the corresponding adjacent nodes through the at least one fibrosis portion in the segmentation image so as to calculate a number of the fibrosis bridges; and determining a score according to a size of the circular fibrosis and the number of the fibrosis bridges.

9. The computer aided fibrosis analyzing method of claim 8, wherein the step of detecting the circular fibrosis according to the segmentation image comprises:

excluding the at least one fibrosis portion, and performing at least one erosion procedure to the at least one cell portion to obtain at least one enclosed portion;

calculating a roundness of the at least one enclosed portion; and determining that the at least one enclosed portion is the circular fibrosis if the roundness of the at least one enclosed portion is greater than a first threshold.

10. The computer aided fibrosis analyzing method of claim 9, wherein the roundness is calculated according to a following equation (1):

$$f_{circ}=4\pi A/p2 \qquad (1)$$

wherein $f_{circ}$ is the roundness, A is an area of the at least one enclosed portion, and P is a perimeter of the at least one enclosed portion.

11. The computer aided fibrosis analyzing method of claim 9, wherein the step of determining the score according to the size of the circular fibrosis and the number of the fibrosis bridges comprises:

dividing a total area of the circular fibrosis by a total area of the at least one cell portion to obtain a first ratio; and determining that the score is a first score if the first ratio is greater than or equal to a second threshold, otherwise determining that the score is a second score, wherein the first score is greater than the second score.

12. The computer aided fibrosis analyzing method of claim 8, wherein the step of determining the score according to a size of the circular fibrosis and the number of the fibrosis bridges comprises:

determining if a second ratio of the number of the fibrosis bridges to an edge number is greater than a third threshold; and determining that the score is a third score if the second ratio is greater than the third threshold, otherwise determining that the score is a fourth score, wherein the third score is greater than the fourth score, the edge number is (3n−3−k), n is a number of the nodes, and k is a number of the nodes on a convex hull formed by the nodes.

13. The computer aided fibrosis analyzing method of claim 8, wherein the steps further comprise:

for each of the portal areas, determining if a third ratio of an area of the at least one fibrosis portion in the portal area to an area of the portal area is greater than a fourth threshold, and determining that the portal area is a portal expansion if the third ratio is greater than the fourth threshold; and determining that the score is a fifth score, a sixth score, or a seventh score according to a number of the portal expansions.

14. The computer aided fibrosis analyzing method of claim 13, wherein the steps further comprise:
- determining that the score is the fifth score if a fourth ratio of the number of the portal expansions to a number of the portal areas is greater than a fifth threshold;
- determining that the score is the sixth score if the fourth ratio is less than or equal to the fifth threshold and greater than zero; and
- determining that the score is the seventh score if the number of the portal expansions is equal to zero, wherein the fifth score is greater than the sixth score which is greater than the seventh score.

15. An electrical device, comprising:
- a memory, configured to store a plurality of instructions; and
- a processor, configured to execute the instructions to perform a plurality of steps:
  - obtaining a medical image, and performing a segmentation algorithm to the medical image to obtain a segmentation image having at least one fibrosis portion and at least one cell portion;
  - detecting circular fibrosis according to the segmentation image;
  - detecting a plurality of portal areas and a plurality of central veins in the medical image;
  - taking the portal areas and the central veins as a plurality of nodes, and taking connection between the nodes as edges to form a graph;
  - transforming the graph into a tree structure which indicates corresponding adjacent nodes of each of the nodes;
  - for each of the nodes, determining if the node is connected to the corresponding adjacent nodes through the at least one fibrosis portion in the segmentation image so as to calculate a number of the fibrosis bridges, and
  - determining a score according to a size of the circular fibrosis and the number of the fibrosis bridges.

* * * * *